United States Patent
Vandervalk

(10) Patent No.: US 9,188,672 B2
(45) Date of Patent: Nov. 17, 2015

(54) ULTRASONIC MEASURING GAUGE

(75) Inventor: Leon Vandervalk, Brockville (CA)

(73) Assignee: DEFELSKO CORPORATION, Ogdensburg, NY (US)

( * ) Notice: Subject to any disclaimer, the term of this patent is extended or adjusted under 35 U.S.C. 154(b) by 826 days.

(21) Appl. No.: 13/447,103

(22) Filed: Apr. 13, 2012

(65) Prior Publication Data

US 2013/0272094 A1    Oct. 17, 2013

(51) Int. Cl.
| | |
|---|---|
| *G01N 29/265* | (2006.01) |
| *G01S 15/88* | (2006.01) |
| *G01B 17/02* | (2006.01) |
| *G01N 29/04* | (2006.01) |
| *G01S 7/52* | (2006.01) |
| *G01S 7/62* | (2006.01) |

(52) U.S. Cl.
CPC .............. *G01S 15/88* (2013.01); *G01B 17/02* (2013.01); *G01N 29/04* (2013.01); *G01S 7/52004* (2013.01); *G01S 7/6272* (2013.01)

(58) Field of Classification Search
CPC ............ G01N 29/069; G01N 29/2437; G01N 29/265; G01N 29/4463; G01N 2291/011; G01N 2291/0231; G01N 2291/0289; G01N 2291/02854
USPC .................................... 73/602, 633, 634, 641
See application file for complete search history.

(56) References Cited

U.S. PATENT DOCUMENTS

| | | | | |
|---|---|---|---|---|
| 2004/0117133 A1* | 6/2004 | Burkhardt et al. | ............... | 702/35 |
| 2004/0117134 A1* | 6/2004 | Burkhardt et al. | ............... | 702/35 |
| 2008/0156096 A1* | 7/2008 | Kollgaard et al. | ............... | 73/577 |
| 2010/0251822 A1* | 10/2010 | Isobe et al. | ....................... | 73/606 |
| 2011/0000299 A1* | 1/2011 | Isobe et al. | ....................... | 73/625 |

* cited by examiner

*Primary Examiner* — Laura Martin
*Assistant Examiner* — Rose M Miller
(74) *Attorney, Agent, or Firm* — Buchanan Ingersoll & Rooney PC

(57) ABSTRACT

An ultrasonic measuring gauge includes a probe configured to be moved along a surface of a material to be measured, transmit ultrasonic waves to the material, and receive ultrasonic waves reflected from the material. The gauge also includes a processing unit and an input unit. The processing unit is configured to operate according to one of two different modes of operation based on an input received by the input unit. In a first mode of operation, the probe determines the thickness at portions between the first and second locations on the surface of the material at which the probe is coupled to the material regardless of whether the probe is continuously physically coupled between the two locations. In a second mode of operation, the processing unit determines a corresponding thickness of the material at each portion between two locations when the probe is continuously physically coupled between the two locations.

25 Claims, 4 Drawing Sheets

ULTRASONIC MEASURING GAUGE

FIELD

The present disclosure relates to an ultrasonic measuring gauge. More particularly, the present disclosure relates to an ultrasonic measuring gauge for measuring the thickness of a material as well as investigating the existence of flaws in the material.

BACKGROUND

Ultrasonic measuring gauges are commonly used to measure the thickness of a material, and to determine whether there are any structural flaws in the material. Such gauges can be used for, example, to measure the effects of corrosion or erosion on tanks, pipes or any solid material where access is limited to one side of the material.

FIG. 1 illustrates an example of the structural features of a known ultrasonic gauge 110. The known gauge 110 includes a probe part 114 at a lower end of the gauge which enables a probe 116 to be connected to the gauge 110. At an opposite end of the gauge 110, a display 115 is arranged for reading out measurements or other data. Switches 112, 113, 117 are also provided on the gauge 110 for controlling the operation of the gauge 110. The switches 112, 113 and 117 are shown external to the display 115 in FIG. 1. However, the switches 112, 113 and 117 and other controls can be provided on the display 115 in the form of a touch-screen display.

The probe 116 includes a transducer for transmitting ultrasonic waves to a surface of a material to be measured, and receiving ultrasonic waves reflected back from the material. Processing circuitry comprised in the gauge 110 computes the thickness of the material based on the transmitted and received ultrasonic waves. The existence of structural flaws in the material can be determined based on the measured thickness of one part of the material, as compared with the relative thickness of other parts of the material. For example, during a scanning operation, the processing circuitry within the gauge 110 can compile aggregate data including a maximum thickness value and a minimum thickness value while the probe 116 is dragged across the material in continuous, uninterrupted physical contact with the material. U.S. Pat. No. 5,009,103 is an example of a known ultrasonic measuring gauge for measuring the thickness of a material. The entire disclosure of U.S. Pat. No. 5,009,103 is incorporated by reference in its entirety.

During a measurement operation, a coupling gel is commonly applied to the surface of the material to be tested. The gel provides a medium through which ultrasonic waves can travel from the probe 116 to the material. During scanning operations involving rough and/or scaly surfaces of the material, the probe 116 is dragged across the surface of the material while the processing circuitry in the gauge 110 analyzes ultrasonic reflections from the material that are propagated back to the processing circuitry via the probe 116. During such scanning operations, the probe 116 is in physical contact with the material via the coupling gel. However, during scanning operations, the probe 116 can be become physically decoupled, that is physically separated, from the material, either due to the rough and/or scaly surface of the material or due to user operation.

FIG. 2 illustrates an example of a scanning operation using such an ultrasonic gauge 110 on a material having a non-uniform surface. For clarity of illustration, only the probe 116 of the gauge 110 is illustrated in FIG. 2 for scanning the surface of a material 210. As shown at point A in FIG. 2, the probe 116 is physically coupled to the material 210 and thus the processing circuitry of the gauge 110 will be able to determine the thickness of the material 210 at point A due to the reflection of ultrasonic waves from the material 210 at point A. At point B, however, the probe 116 becomes physically decoupled (i.e., physically separated) from the material 210 due to the ridge and subsequent crevice at point B. As noted above, the processing circuitry of the gauge 110 is configured to maintain continuous readings while the probe 116 is in continuous, uninterrupted physical contact with the material 210. For example, it may be desirable to determine the maximum and minimum thicknesses of the material between points A and E of FIG. 2. However, because the probe 116 has become physically decoupled from the material 210 at point B, the processing circuitry of the gauge 110 may reset the measurement session, such that only the maximum and minimum values between points A and B are recorded. Similarly, even if the probe 116 is physically coupled again to the material 210 after point B, the operator may physically decouple the probe 116 from the material 210 at point C due to the ridge at point C. Such a decoupling will again result in the processing circuitry to restart a new measurement session between only points B and C. At point D, the probe 116 can be physically re-coupled to the material 210 and obtain continuous measurements between points D and E. However, due to the physical decoupling of the probe 116 at points B and C, the processing circuitry of the gauge 110 may output three independent measurement sessions, that is, (i) from point A to point B, (ii) from point B to point C, and (iii) from point D to point E. Accordingly, if it desired to measure the maximum and minimum thicknesses continuously from points A to E, erroneous indications may result due to the physical decoupling of the probe 116 from the material 210.

SUMMARY

An exemplary embodiment of the present disclosure provides an ultrasonic measuring gauge which includes a probe configured to be moved along a surface of a material to be measured, to transmit ultrasonic waves to the material, and to receive ultrasonic waves reflected from the material. The exemplary ultrasonic measuring gauge also includes an input unit configured to receive a first operation instruction to continuously measure the thickness of the material independent of whether the probe is physically coupled to the material. In addition, the exemplary ultrasonic measuring gauge includes a processing unit configured to operate according to a first mode of operation in which the processing unit is configured to maintain a first continuous measurement session of the material between a first location on the surface of the material and a second location on the surface of the material distant from the first location, regardless of whether the probe becomes physically decoupled from the material between the first and second locations, and to determine a corresponding thickness of the material at a plurality of portions of the material along the surface of the material between the first and second locations when the probe is physically coupled to the material at the plurality of portions, based on the reflected waves received by the probe at the plurality of portions, respectively.

An exemplary embodiment of the present disclosure provides a method of operating an ultrasonic measuring gauge, which includes a processing unit configured to control operations of the ultrasonic measuring gauge, an input unit configured to receive an operation instruction, and a probe configured to be moved along a surface of a material to be measured, to transmit ultrasonic waves to the material, and to receive ultrasonic waves reflected from the material. The exemplary method includes receiving, by the input unit, an operation instruction indicating that the processing unit is to continuously measure the thickness of the material independent of whether the probe is physically coupled to the material. The exemplary method also includes operating the processing unit of the ultrasonic measuring gauge according to a first mode of operation in which the processing unit maintains a first continuous measurement session of the material between a first location on the surface of the material to a second location on the surface of the material distant from the first location, regardless of whether the probe becomes physically decoupled from the material between the first and second locations. The exemplary method also includes determining, in the processing unit under the first mode of operation, a corresponding thickness of the material at a plurality of portions of the material along the surface of the material between the first and second locations when the probe is physically coupled to the material at the plurality of portions, based on the reflected waves received by the probe at the plurality of portions, respectively.

An exemplary embodiment of the present disclosure provides a non-transitory computer-readable recording medium having a computer program recorded thereon and executable by a processor of an ultrasonic measuring gauge. The ultrasonic measuring gauge includes an input unit configured to receive an operation instruction, and a probe configured to be moved along a surface of a material to be measured, to transmit ultrasonic waves to the material, and to receive ultrasonic waves reflected from the material. The computer program causes the processor to receive, by the input unit, an operation instruction indicating that the processor is to continuously measure the thickness of the material independent of whether the probe is physically coupled to the material. The computer program also causes the processor to, upon receiving the operation instruction, operate according to a first mode of operation in which the processor maintains a first continuous measurement session of the material between a first location on the surface of the material to a second location on the surface of the material distant from the first location, regardless of whether the probe becomes physically decoupled from the material between the first and second locations. The computer program also causes the processor to determine, under the first mode of operation, a corresponding thickness of the material at a plurality of portions of the material along the surface of the material between the first and second locations when the probe is physically coupled to the material at the plurality of portions, based on the reflected waves received by the probe at the plurality of portions, respectively.

BRIEF DESCRIPTION OF THE DRAWINGS

Additional refinements, advantages and features of the present disclosure are described in more detail below with reference to exemplary embodiments illustrated in the drawings, in which.

DETAILED DESCRIPTION

Exemplary embodiments of the present disclosure solve the drawbacks noted above. An exemplary embodiment of the present disclosure provides an ultrasonic measuring gauge which can maintain a continuous, uninterrupted measurement session even when a probe becomes physically decoupled from the material to be measured.

Figure 3:
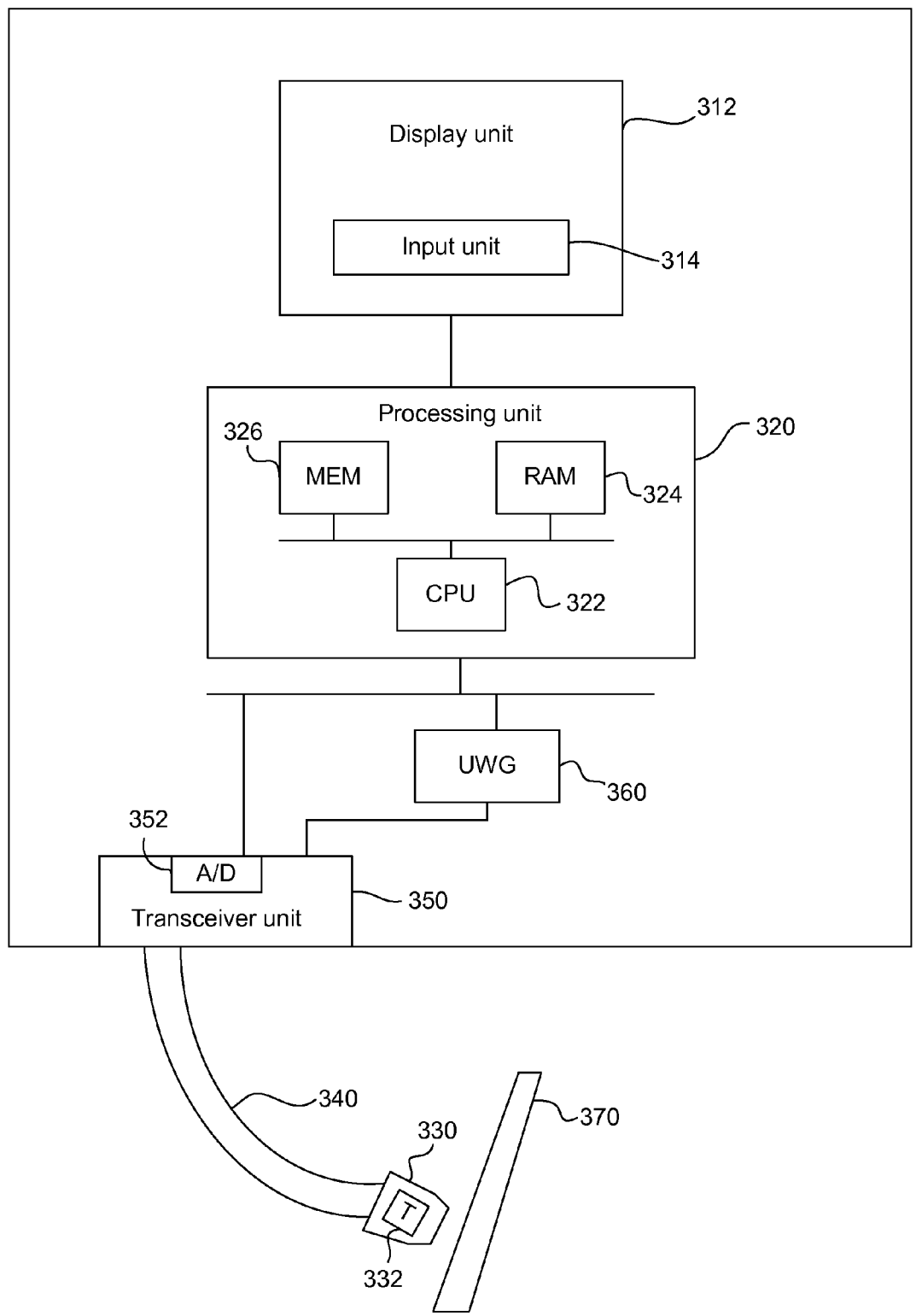
FIG. 3 illustrates a block diagram of an ultrasonic measuring device according to an exemplary embodiment of the present disclosure.

FIG. 3 illustrates a block diagram of an ultrasonic measuring device 300 according to an exemplary embodiment of the present disclosure. The ultrasonic measuring device 300 includes a housing 310 in which are provided a display unit 312, an input unit 314, a processing unit 320, a transceiver unit 350, and an ultrasonic wave generator 360. The display unit 312 is configured to display user-selectable operation instructions, measurement results, and any other information for the operation of the ultrasonic measuring device 300. In the example of FIG. 3, the input unit 314 is illustrated as being comprised in the display unit 312. For example, the input unit 314 could be a touch-screen display in which a user can enter input commands via the display unit 312. However, it is conceived that the input unit 314 may be provided separate from the display unit 312 and include physical input means such as keys, trackpads, buttons, etc.

The processing unit 320 includes a computer processor (general-purpose or application specific) that is configured to control the operations of the ultrasonic measuring gauge 300. In the example of FIG. 3, the processing unit 320 is illustrated as including a non-transitory, non-volatile memory (MEM) 326 on which a computer program and/or computer-readable instructions is/are tangibly recorded. The processor (CPU) 322 is configured to execute the program and/or instructions recorded on the memory 326 to carry out the operations and functions of the ultrasonic measuring gauge 300 as described herein. The processing unit 320 can also include a working memory such as a random access memory (RAM) 324 to utilize while performing its functions. The RAM 324 and MEM 326 can be provided separately from the processor 322, for example, in a different physical unit from the processor 322. The MEM 326 may be any type of non-volatile memory such as a read only memory (ROM), hard disk drive, flash memory, optical memory, etc.

The ultrasonic measuring gauge 300 also includes a probe 330, a cable 340 and a transceiver unit 350. The probe 330 can include a transducer, such as a piezoelectric transducer, which is configured to transmit ultrasonic waves to a material 370 to be measured, and to receive ultrasonic waves reflected from the material 370. The transducer 332 can generate measurement signals representing the reflected ultrasonic waves. For example, the transducer 332 can convert the reflected ultrasonic waves into an analog signal representing the intensity and/or frequency of the ultrasonic waves reflected from the material 370. The cable 340 provides a communication interface between the transceiver unit 350 and the probe 330. The transceiver unit 350 is configured to exchange signals between the probe 330 and the processing unit 320. The transceiver unit 350 may, for example, include an analog-to-digital converter 352 to convert analog signals received from the transducer 332 into digital signals to be interpreted by the processing unit 320, and convert digital signals into analog commands for controlling the transducer 332. The ultrasonic measuring gauge 300 also includes an ultrasonic wave generator 360 configured to generate the ultrasonic waves transmitted from the probe 330 to the material.

In accordance with an exemplary embodiment, the probe 330 can include a dual element transducer. In the case of a dual element transducer, the transceiver unit 350 may not be required. One of the dual elements of the transducer sends out ultrasound waves, while the other dual element receives ultrasound waves reflected from the material 370.

To begin measuring the thickness of the material 370, a user can physically couple the probe 330 to the surface of the material 370. As used herein, the term "coupled" means physically connected, and the term "decoupled" means physically disconnected. Accordingly, as used herein, when the probe 330 is described as being "physically coupled" to the material 370, the probe 330 is physically connected to the material 370. Conversely, when the probe 330 is described as being "decoupled" from the material 370, the probe 330 is no longer in physical contact with the material 370. As noted above, a coupling gel may be applied to the surface of the material 370 to be tested. If the probe 330 is in physical contact with the coupling gel applied to the surface of the material 370, then the probe 330 is physically coupled to the material 370. Conversely, if the probe 330 is not in physical contact with the coupling gel applied to the surface of the material 370, then the probe is decoupled from the material 370. In accordance with an exemplary embodiment, the processing unit 320 determines whether the probe 330 is physically decoupled from the material 370 by comparing a particular value of the reflected waves received by the probe 330 to a threshold value. For example, the processing unit 320 can be configured to maintain a threshold value for the amount of time which lapses between when the reflected waves are received in comparison to when the probe 330 transmitted the ultrasonic waves, a value for the intensity and/or frequency of the reflected waves received from the material 370, etc.

Figure 1:
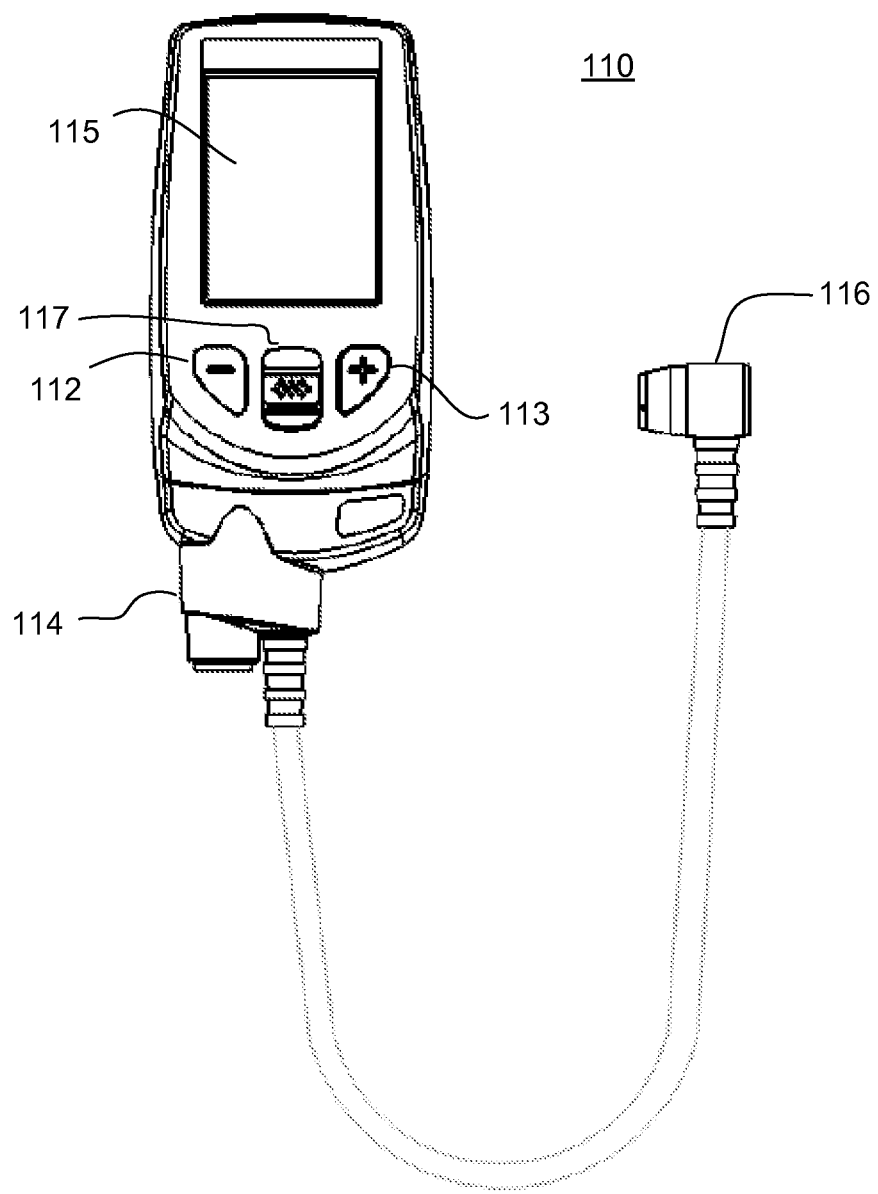
FIG. 1 illustrates a known ultrasonic measuring device.
Figure 2:
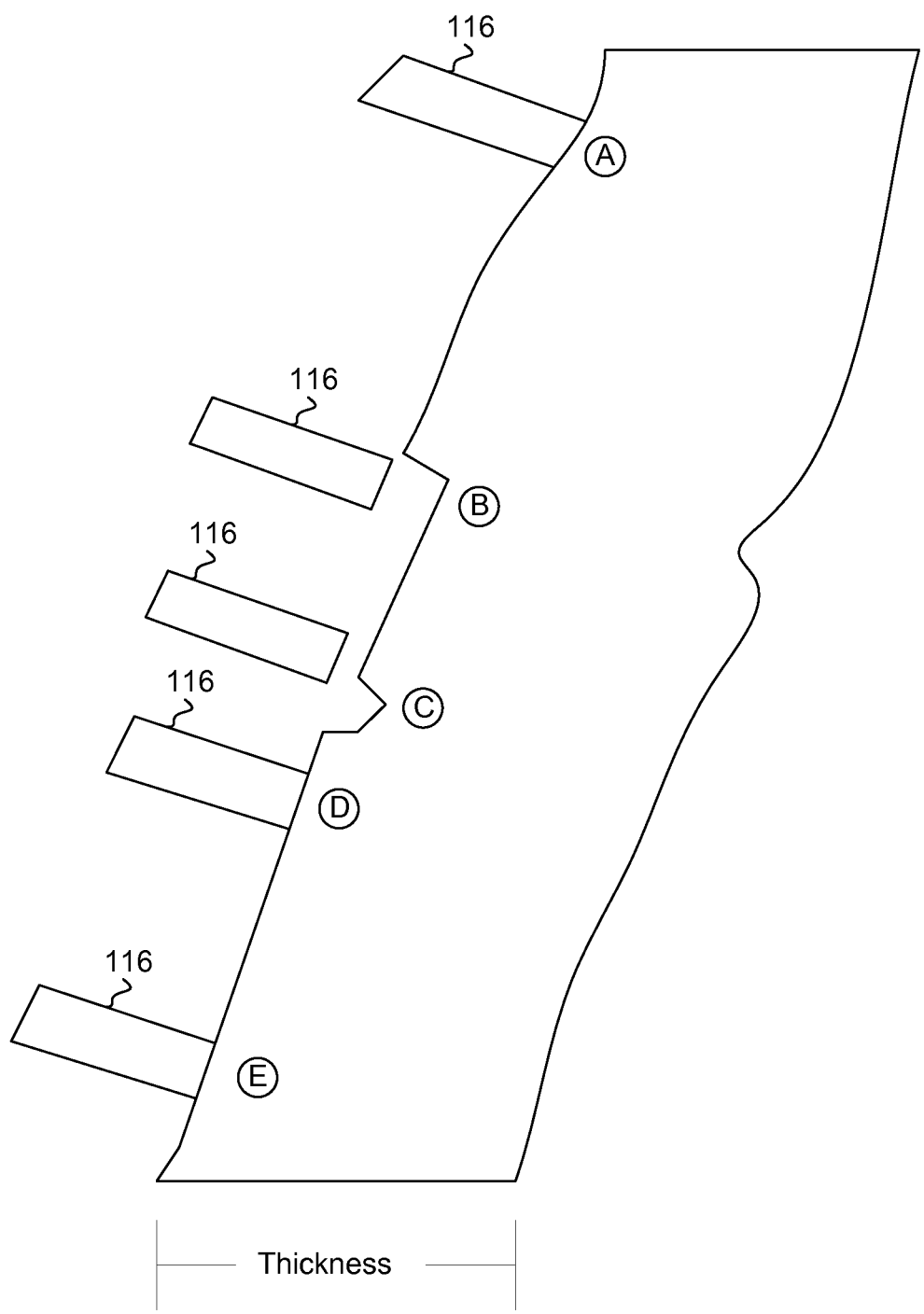
FIG. 2 illustrates an example of a scanning operation on a surface of a material having a non-uniform surface.

The processing unit 320 is configured to operate according to two different modes of operation, based on a specific operation instruction received by the input unit 314. A user can input the operation instruction to the input unit 314 by manually specifying the operation instruction from a list of selectable options, or by pressing a predetermined key assigned to that operation instruction, for example. Numerical adjectives such as "first" and "second" are used herein to distinguish between different features of the present disclosure. The use of such numerical adjectives is not intended to imply or connote a specific sequence in any way. For instance, a feature described with the adjective "first" can be performed after a feature described with the adjective "second", and vice versa. In addition, the term "between" is used herein to describe a range of portions on the surface of the material 370 between two locations (e.g., points A and E as illustrated in FIG. 2) on the surface of the material 370. As used herein, the term "between" is intended to include and encompass the two locations described in a range of portions of the surface of the material. Therefore, with respect to the example of FIG. 2, the phrase "between locations A and E" is intended to include locations A and E, and the portions therebetween.

With reference to the example of FIG. 2, in a mode of operation which will hereinafter be referred to as a "continuously physically coupled" (CPC) mode, the processing unit 320 is configured to maintain, for the CPC mode of operation, a continuous measurement session of the material 210 from a first location (e.g., point A) on the surface of the material 210 to a second location (e.g., point B) on the surface of the material 210. The first and second locations are different locations on the surface of the material 210 and thus are distant from each other by some degree. In the CPC mode of operation, the processing unit 320 maintains the continuous measurement session for the CPC mode of operation when the probe 330 is continuously physically coupled to the surface of the material between the first and second locations. For example, with reference to FIG. 2, the processing unit 320 can maintain a continuous measurement session for the CPC mode of operation between points A and points B, while the probe 330 is continuously physically coupled to the material 210 between points A and B. Provided that the probe 330 is continuously physically coupled between points A and B, the processing unit 320 can determine a corresponding thickness of the material at each portion of the material 210 between points A and B based on the reflected ultrasonic waves received by the probe 330 at each of those portions, respectively. Similarly, with respect to FIG. 2, the processing unit 320 can maintain a continuous measurement session for the CPC mode of operation between points B and C, and between points D and E, provided that the probe is continuously physically coupled to the surface of the material 210 between these respective points. In addition to obtaining thickness measurements at each point at which the probe 330 is physically coupled to the material 210, the processing unit 320 can also obtain and generate other measurements, such as the minimum and/or maximum thickness values obtained during the continuous measurement session, a range of thickness over time, etc.

However, when the probe 330 becomes decoupled from the material 210, the continuous measurement session between those two points of measurement ends for the CPC mode of operation. This can result in erroneous or incomplete measurement results. For example, if the probe 330 is decoupled from the material 210 at points B and C according to the example of FIG. 2, then there would not be a continuous measurement session from points A to E of the material 210. That is, if the probe 330 is decoupled at points B and C in the example of FIG. 2, and the user desires to know the minimum and maximum thickness values between points A and E, the user would obtain, according to the CPC mode of operation, a first set of results based on a continuous measurement session between points A and B, a second set of results based on a continuous measurement session between points B and C, and a third set of results based on a continuous measurement session between points D and E.

To obviate this drawback, the present disclosure provides a mode of operation which may hereinafter be referred to as a "continuous electronic" (CE) mode, in which the processing unit 320 interprets the probe 330 as being continuously physically coupled to the material 210, 370 even if the probe 330 is decoupled from the material. This mode of operation is referred to as a continuous electronic mode, because the processing unit 330 is configured to interpret, in determining measurement results, the probe 330 as being continuously physically coupled to the material 210, 370, even though the probe 330 may become decoupled from the material 210, 370 during a measurement session. In effect, under this electronic mode of operation, the processing unit 320 electronically (i.e., by its computational operation) interprets the probe 330 as being electronically coupled to the material 210, 370 even if the probe 330 is decoupled from the material 210, 370, either due to user operation or a change in contour of the surface of the material 210, 370.

The processing unit 320 is configured to operate according to the CE mode of operation when the input unit 314 receives an operation instruction indicating that the processing unit 320 is to continuously measure the thickness of the material 210, 370 independent of whether the probe 330 is physically coupled to the material 210, 370. As noted above, the input unit 314 can be configured to receive the operation instruction according to a number of different techniques, such as the selection of the operation instruction from a list of selectable options, by pressing a predetermined key, etc.

When the input unit 314 receives the operation instruction indicating that the processing unit 320 is to operate according to the CE mode of operation, the processing unit 320 maintains a different continuous measurement session than the continuous measurement session described above for the CPC mode of operation. In the CE mode of operation, the processing unit 320 maintains a continuous measurement session of the material 210, 370 between first and second locations (e.g., points A and E of FIG. 2) regardless of whether the probe 330 become physically decoupled from the material between the first and second locations (e.g., points A and E of FIG. 2). Therefore, with reference to the example of FIG. 2, the processing unit 320, when operating according to the CE mode of operation, will maintain a continuous measurement session between points A and E, even if the probe 330 is decoupled at points B and C. Under the CE mode of operation, the processing unit 320 is configured to determine a corresponding thickness of the material 210, 370 at a plurality of portions of the material 210, 370 along the surface of the material 210, 370 when the probe 330 is physically coupled to the material those plurality of portions, based on the reflected waves received by the probe 330 at those plurality of portions. Accordingly, with reference to the example of FIG. 2, under the CE mode of operation, the processing unit 320 is configured to maintain a continuous measurement session between points A and E and obtain individual measurements at each point between points A and E at which the probe 330 is physically coupled to the material 210.

The CE mode of operation provides a number of advantages. For example, the user can make multiple passes between various points of a material to be measured, and not have to actively concentrate on ensuring that the probe 330 is physically coupled to the material. The user can therefore focus on the material itself, rather than the instrument, or can focus more closely on the measurement results displayed on the display unit 312. In addition, by providing a mechanism which essentially controls the processing unit 320 to become electronically coupled to the material, even if the probe 330 is not itself physically coupled continuously to all the measurement points, it provides higher accuracy and faster scanning, since the user does not have to stop and record between different scanning operations.

It is to be understood that the present disclosure is not limited to the example of FIG. 2 in which the measurement is intended to start at point A and end at point E. The user can apply the probe 330 in all different directions, including a reversal of a previously scanned direction, and obtain a set of continuous measurement results in one session while the processing unit 320 is designated to operate according to the CE mode of operation. Under the CE mode of operation, the first location (i.e., the beginning point of the continuous session) can be the point on the material at which the probe 330 is first detected to be coupled to the material 210, 370. When operating according to the CE mode of operation, the processing unit 320 can determine the second location (i.e., the end point of the continuous session) according to a number of different techniques. For example, when the processing unit 320 is operating according to the CE mode of operation, the input unit 314 can receive another operation instruction indicating that the processing unit 320 is to return to the CPC mode of operation. In this case, the processing unit 320 can determine a portion on the surface of the material 210, 370 constituting the second location on the surface of the material when the input unit receives the operation instruction to return to the CPC mode of operation. When the probe 330 is physically decoupled from the material 210, 370 when the input unit 314 receives the operation instruction to return to the CPC mode of operation, the processing unit 320 can determine that the second location is constituted by one of the plurality of portions on the surface of the material 210, 370 at which the probe last received a reflected wave during the continuous measurement session under the CE mode of operation. When the probe 330 is physically coupled to the material 210, 370 when the input unit 314 receives the operation instruction to return to the CE mode of operation, the processing unit 320 can determine that the second location is constituted by one of the plurality of portions on the surface of the material 210, 370 at which the probe is physically decoupled from the material 210, 370.

In accordance with an exemplary embodiment, when the processing unit 320 is operating according to the CE mode of operation, the processing unit is configured to end (e.g., complete) the continuous measurement session for the CE mode of operation when the processing unit 320 determines that the probe 330 is continuously decoupled from the material 210, 370 for a predetermined period of time (e.g., a period of seconds). For example, if the processing unit 320 is operating according to the CE mode of operation and obtaining measurements at portions on the material 210, 370 between two locations of the locations 210, 370 when the probe 330 is respectively coupled at those portions during a continuous measurement session, the processing unit 320 can determine to complete that measurement session if the processing unit 320 determines that the probe 330 has been physically decoupled from the material for a predetermined period of time, such as five seconds, for example. The processing unit 320 can be configured by a user operation of the input unit 314 to specify this predetermined period of time.

Figure 4A:
FIGS. 4A-4C illustrate examples of display screens output by a display of the ultrasonic measuring device illustrated in FIG. 3.
Figure 4B:
Figure 4C:
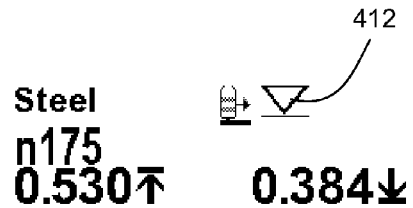

When the processing unit 320 is operating according to the CE mode of operation, the processing unit 320 can record, in a non-transitory recording medium such as MEM 326, at least one of minimum and maximum values of the thickness of the material measured among the corresponding portions of the material between the first and second locations during that continuous measurement session for the CE mode of operation. In addition, the display unit 312 can be configured, under the control of the processing unit 320, to display thickness measurements determined by the processing unit 320 at any point between the first and second locations, as well as the determined maximum and/or minimum values for that continuous measurement session. FIG. 4A illustrates an example of a display output from the display unit 312 indicating a thickness measurement 402 at the portion of the material on which the probe 330 is applied, as well as a maximum thickness measurement 404 and a minimum thickness measurement 406 during that continuous measurement session. In addition, the processing unit 320 is configured to control the display unit 312 to display an indication identifying when the processing unit is operating to the CPC mode of operation or the CE mode of operation, as well as whether the probe 330 is currently coupled to or decoupled from the material. For instance, in the example of FIG. 4A, the indication 408 identifies that the processing unit 320 is operating according to the CPC mode of operation, and that the probe 330 is currently coupled to the material (darkened triangle). In the example of FIG. 4B, the indication 410 identifies that the processing unit 320 is operating according to the CE mode of operation (line below triangle), and that the probe 330 is currently coupled to the material (darkened triangle). In the example of FIG. 4C, the indication 412 identifies that the processing unit 320 is operating according to the CE mode of operation (line below triangle), and that the probe 330 is currently decoupled from the material (un-darkened triangle).

In accordance with an exemplary embodiment, the ultrasonic measuring gauge is dimensioned as a portable handheld device. For example, a user can operate the probe 330 using one hand while holding the housing 310 in the other hand. Alternatively, the housing 310 can include a securing mechanism such as a foldable stand on which to rest on a surface such as a table while the user operates the probe 330 to determine the thickness of a material 370 to be measured.

In accordance with an exemplary embodiment, when the processing unit 320 is operating according to either of the above-described CPC or CE mode of operation, the input unit 314 is configured to receive an operation instruction to switch the mode of operation of the processing unit 320 to the opposite mode of operation in which the processing unit is currently operating. For example, when the processing unit 320 is operating to the CPC mode of operation in which a continuous measurement session is maintained when the probe 330 is continuously physically coupled to the material 210, 370, a user can provide an input via the input unit 314 to switch the mode of operation of the processing unit 320 to the CE mode of operation in which the processing unit 320 maintains a different continuous measurement session between two locations on the surface of the material 210, 370, regardless of whether the probe 330 is continuously physically coupled between the two locations on the material 210, 370, and vice versa.

An exemplary embodiment of the present disclosure also provides a method of operating the ultrasonic measuring gauge. The exemplary method of the present disclosure includes operating the processing unit 320 of the ultrasonic measuring gauge 300 according to the CPC mode of operation in which the processing unit 320 maintains, for the CPC mode of operation, a continuous measurement session of the material from a first location on the surface of the material to a second location on the surface of the material distant from the first location, when the probe 330 is continuously physically coupled to the surface of the material between the first and second locations. The exemplary method also includes determining, in the processing unit 320 under the CPC mode of operation, a corresponding thickness of the material at each portion of the material along the surface of the material between the first and second locations based on the reflected ultrasonic waves received by the probe at each portion of the material between the first and second locations, respectively, when the probe 330 is continuously physically coupled to the surface of the material between the first and second locations. The exemplary method also includes receiving, by the input unit 314, an operation instruction indicating that the processing unit 320 is to continuously measure the thickness of the material independent of whether the probe 330 is physically coupled to the material. In addition, the exemplary method includes operating the processing unit 320, upon receiving the operation instruction, according to the CE mode of operation in which the processing unit 320 maintains, for the CE mode of operation, a continuous measurement session of the material between the first and second locations of the material regardless of whether the probe 330 becomes physically decoupled from the material between the first and second locations. Furthermore, the exemplary method includes determining, in the processing unit 320 under the CE mode of operation, a corresponding thickness of the material at a plurality of portions of the material along the surface of the material between the first and second locations when the probe 330 is physically coupled to the material at the plurality of portions, based on the reflected waves received by the probe 330 at the plurality of portions, respectively.

In addition, an exemplary embodiment of the present disclosure provides a non-transitory computer-readable recording medium (e.g., MEM 326) having a computer program recorded thereon that causes the processor 322 of the ultrasonic measuring device 300 to carry out operations corresponding to the above-described exemplary method.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. An ultrasonic measuring gauge comprising:
   a probe configured to be moved along a surface of a material to be measured, to transmit ultrasonic waves to the material, and to receive ultrasonic waves reflected from the material;
   an input unit configured to receive a first operation instruction to continuously measure the thickness of the material independent of whether the probe is physically coupled to the material; and
   a processing unit configured to
   determine whether the probe is physically coupled or physically decoupled from the material based on the reflected ultrasonic waves received by the probe from the material,
   when the input unit receives the first operation instruction, operate according to a first mode of operation in which the processing unit is configured to maintain a first continuous measurement session of the material between a first location on the surface of the material and a second location on the surface of the material distant from the first location, regardless of whether the probe becomes physically decoupled from the material between the first and second locations, and
   determine a corresponding thickness of the material at a plurality of portions of the material along the surface of the material between the first and second locations when the probe is physically coupled to the material at the plurality of portions, based on the reflected waves received by the probe at the plurality of portions, respectively.

2. The ultrasonic measuring gauge according to claim 1, wherein the processing unit is configured to determine an intensity of the reflected waves received by the probe, and to determine when the probe is physically decoupled from the material by comparing the determined intensity of the reflected waves received by the probe to a threshold value.

3. The ultrasonic measuring gauge according to claim 1, wherein the probe includes a transducer configured to receive the reflected ultrasonic waves, and generate measurement signals representing the received reflected ultrasonic waves.

4. The ultrasonic measuring gauge according to claim 3, comprising an analog to digital converter configured to receive the measurement signals generated by the transducer in analog format, to convert the received measurement signals to a digital format, and to output the converted measurement signals to the processing unit.

5. The ultrasonic measuring gauge according to claim 3, wherein the transducer is a piezoelectric transducer.

6. The ultrasonic measuring gauge according to claim 3, wherein the transducer comprises a dual element transducer including a first component configured to transmit ultrasonic waves to the material to be measured, and a second component configured to receive the reflected ultrasonic waves from the material.

7. The ultrasonic measuring gauge according to claim 1, comprising:
a housing;
a display unit configured to display measurement results;
a transceiver unit configured to exchange signals between the probe and the processing unit;
an ultrasonic wave generator configured to generate the ultrasonic waves transmitted from the probe; and
a cable configured to communicatively connect the transceiver unit to the probe,
wherein the processing unit, input unit, display unit, transceiver unit and ultrasonic wave generator are comprised in the housing.

8. The ultrasonic measuring gauge according to claim 7, wherein the input unit is comprised in the display unit as a touch-screen input device.

9. The ultrasonic measuring gauge according to claim 7, wherein the transceiver unit comprises an analog to digital converter configured to receive the measurement signals generated by the probe in analog format, to convert the received measurement signals to a digital format, and to output the converted measurement signals to the processing unit.

10. The ultrasonic measuring gauge according to claim 7, wherein the processing unit is configured to control the display unit to display an indication identifying when the processing unit is operating to the first mode of operation or a second mode of operation in which the processing unit maintains a second continuous measurement session of the material between the first and second locations, when the probe is continuously physically coupled to the surface of the material between the first and second locations.

11. The ultrasonic measuring gauge according to claim 1, wherein when the processing unit is operating according to the first mode of operation, the processing unit is configured to record, in a non-transitory recording medium, at least one of minimum and maximum values of the thickness of the material measured among the corresponding portions of the material between the first and second locations.

12. The ultrasonic measuring gauge according to claim 11, comprising:
a display configured to output thickness measurements determined by the processing unit, and to display the determined at least one of maximum and minimum values.

13. The ultrasonic measuring gauge according to claim 12, wherein the display is configured to display an indication identifying whether the probe is physically coupled to the material or whether the probe is decoupled from the material.

14. The ultrasonic measuring gauge according to claim 1, wherein, when the processing unit is operating according to the first mode of operation, the input unit is configured to receive a second operation instruction indicating that the processing unit is to end the first continuous measurement session.

15. The ultrasonic measuring gauge according to claim 14, wherein the processing unit is configured to determine a portion on the surface of the material constituting the second location on the surface of the material when the input unit receives the second operation instruction.

16. The ultrasonic measuring gauge according to claim 15, wherein when the probe is physically decoupled from the material when the input unit receives the second operation instruction, the processing unit is configured to determine that the second location is constituted by one of the plurality of portions on the surface of the material at which the probe last received a reflected wave during the first continuous measurement session.

17. The ultrasonic measuring gauge according to claim 15, wherein when the probe is physically coupled to the material when the input unit receives the second operation instruction, the processing unit is configured to determine that the second location is constituted by one of the plurality of portions on the surface of the material at which the probe is physically decoupled from the material.

18. The ultrasonic measuring gauge according to claim 1, wherein, when the processing unit is operating according to the first mode of operation, the processing unit is configured to end the first continuous measurement session when the processing unit determines that the probe is continuously decoupled from the material for a predetermined period of time.

19. The ultrasonic measuring gauge according to claim 1, wherein the processing unit is configured to operate according to a second mode of operation in which the processing unit is configured to maintain a second continuous measurement session of the material between the first and second locations, when the probe is continuously physically coupled to the surface of the material between the first and second locations, and to determine a corresponding thickness of the material at each portion of the material along the surface of the material between the first and second locations based on the reflected ultrasonic waves received by the probe at each portion of the material between the first and second locations, respectively.

20. The ultrasonic measuring gauge according to claim 19, wherein, when the processing unit is operating according to one of the first mode of operation and the second mode of operation, the input unit is configured to receive a second operation instruction to switch the mode of operation of the processing unit to the opposite mode of operation in which the processing unit is currently operating.

21. The ultrasonic measuring gauge according to claim 1, wherein the ultrasonic measuring gauge is dimensioned as a portable handheld device.

22. A method of operating an ultrasonic measuring gauge, which includes a processing unit configured to control operations of the ultrasonic measuring gauge, an input unit configured to receive an operation instruction, and a probe configured to be moved along a surface of a material to be measured, to transmit ultrasonic waves to the material, and to receive ultrasonic waves reflected from the material, the method comprising:
determining, by the processing unit, whether the probe is physically coupled or physically decoupled from the material based on the reflected ultrasonic waves received by the probe from the material;
receiving, by the input unit, an operation instruction indicating that the processing unit is to continuously measure the thickness of the material independent of whether the probe is physically coupled to the material;
operating the processing unit, upon receiving the operation instruction, according to a first mode of operation in which the processing unit maintains a first continuous measurement session of the material between a first location on the surface of the material and a second location on the surface of the material distant from the first location, regardless of whether the probe becomes physically decoupled from the material between the first and second locations; and
determining, in the processing unit under the first mode of operation, a corresponding thickness of the material at a plurality of portions of the material along the surface of the material between the first and second locations when the probe is physically coupled to the material at the plurality of portions, based on the reflected waves received by the probe at the plurality of portions, respectively.

23. The method according to claim 22, comprising:

operating the processing unit of the ultrasonic measuring gauge according to a second mode of operation in which the processing unit maintains a second continuous measurement session of the material between the first and second locations, when the probe is continuously physically coupled to the surface of the material between the first and second locations; and determining, in the processing unit under the second mode of operation, a corresponding thickness of the material at each portion of the material along the surface of the material between the first and second locations based on the reflected ultrasonic waves received by the probe at each portion of the material between the first and second locations, respectively, when the probe is continuously physically coupled to the surface of the material between the first and second locations.

24. A non-transitory computer-readable recording medium having a computer program recorded thereon and executable by a processor of an ultrasonic measuring gauge, wherein the ultrasonic measuring gauge includes an input unit configured to receive an operation instruction, and a probe configured to be moved along a surface of a material to be measured, to transmit ultrasonic waves to the material, and to receive ultrasonic waves reflected from the material, and wherein the computer program causes the processor to carry out operations comprising:

determine whether the probe is physically coupled or physically decoupled from the material based on the reflected ultrasonic waves received by the probe from the material;

receive, from the input unit, an operation instruction indicating that the processor is to continuously measure the thickness of the material independent of whether the probe is physically coupled to the material;

upon receiving the operation instruction, operate according to a first mode of operation in which the processor maintains a second continuous measurement session of the material between a first location on the surface of the material and a second location on the surface of the material distant from the first location, regardless of whether the probe becomes physically decoupled from the material between the first and second locations; and determine, under the first mode of operation, a corresponding thickness of the material at a plurality of portions of the material along the surface of the material between the first and second locations when the probe is physically coupled to the material at the plurality of portions, based on the reflected waves received by the probe at the plurality of portions, respectively.

25. The non-transitory computer-readable recording medium according to claim 24, wherein the computer program causes the processor to execute operations comprising:

operate according to a second mode of operation in which the processor maintains a second continuous measurement session of the material between the first and second locations, when the probe is continuously physically coupled to the surface of the material between the first and second locations; and determine, under the second mode of operation, a corresponding thickness of the material at each portion of the material along the surface of the material between the first and second locations based on the reflected ultrasonic waves received by the probe at each portion of the material between the first and second locations, respectively, when the probe is continuously physically coupled to the surface of the material between the first and second locations.

* * * * *